Figure 1:
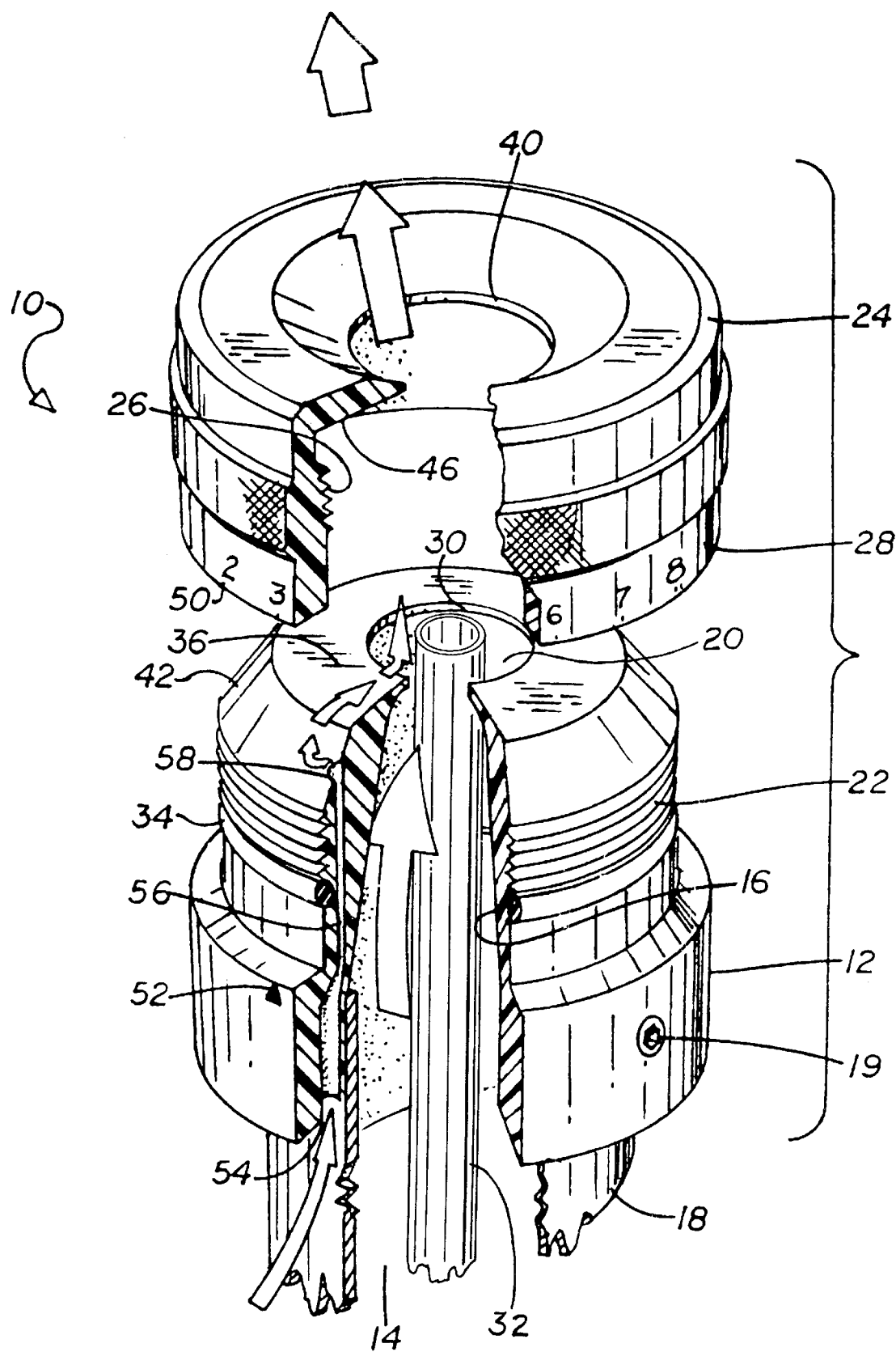

United States Patent
Resch et al.

[11] Patent Number: 6,076,748
[45] Date of Patent: Jun. 20, 2000

[54] ODOR CONTROL ATOMIZER UTILIZING OZONE AND WATER

[76] Inventors: Darrel R. Resch, 294 Canaveral Beach Blvd., Cape Canaveral, Fla. 32920; Elisha W. Erb, 94 Harvard St., Leominster, Mass. 01453

[21] Appl. No.: 09/072,467

[22] Filed: May 4, 1998

[51] Int. Cl.⁷ ...................................................... B05B 7/06
[52] U.S. Cl. ...................... 239/424.5; 239/423; 239/426; 239/427.5; 239/433; 239/434; 261/78.2
[58] Field of Search ..................................... 239/418, 422, 239/423, 424.5, 426, 427.5, 428, 433, 434; 261/78.2

[56] References Cited

U.S. PATENT DOCUMENTS

| | | | |
|---|---|---|---|
| 2,391,422 | 12/1945 | Jackson | 239/424.5 X |
| 2,746,728 | 5/1956 | Pomerleau | 261/78.2 X |
| 3,993,246 | 11/1976 | Erb et al. | |
| 4,018,387 | 4/1977 | Erb et al. | |
| 4,161,281 | 7/1979 | Erb et al. | |
| 4,161,282 | 7/1979 | Erb et al. | |
| 4,261,511 | 4/1981 | Erb et al. | |
| 4,382,044 | 5/1983 | Baumgartner et al. | |
| 4,394,120 | 7/1983 | Golovanov et al. | |
| 4,600,151 | 7/1986 | Bradley | |
| 4,610,760 | 9/1986 | Kirkpatrick et al. | |
| 4,726,760 | 2/1988 | Skoog | 239/422 X |
| 4,907,961 | 3/1990 | Anderson | 239/423 X |
| 5,232,164 | 8/1993 | Resch et al. | |
| 5,256,352 | 10/1993 | Snyder et al. | 261/78.2 |
| 5,297,733 | 3/1994 | Burks et al. | |
| 5,337,961 | 8/1994 | Brambani et al. | |
| 5,337,962 | 8/1994 | Erb et al. | |
| 5,374,164 | 12/1994 | Schulz | |
| 5,400,972 | 3/1995 | Maier et al. | |
| 5,427,317 | 6/1995 | Huttlin | |
| 5,431,861 | 7/1995 | Nagahiro et al. | 261/140.1 |
| 5,513,801 | 5/1996 | Huhne et al. | |
| 5,567,141 | 10/1996 | Joshi et al. | |
| 5,575,341 | 11/1996 | Baker et al. | |
| 5,873,524 | 2/1999 | Bodelin et al. | 239/423 X |

*Primary Examiner*—Andres Kashnikow
*Assistant Examiner*—Robin O. Evans
*Attorney, Agent, or Firm*—Julian C. Renfro

[57] ABSTRACT

A purification device utilizing ozone, this device comprising a body member having an internal passage through which propellant gas is constrained to flow under pressure, with the internal passage forming an outlet at a downstream location in the body member. Liquid is supplied in limited quantities to the propellant gas in the internal passage, with the introduction of the liquid into the propellant gas causing thin ribbons and threads of liquid to flow into and with the gas flowing out of the outlet and to break into fine particles. An ozone supplying conduit is disposed in a central location in the outlet, with the conduit arranged to emit ozone into the propellant gas at a location near the outlet and to create a turbulent propellant gas region downstream of the ozone conduit. The propellant gas flows around the ozone conduit at a substantial velocity and thus serves to induce the flow of ozone from the conduit. The position of the outlet of the ozone conduit with respect to the thin ribbons and threads of liquid being such that the thin ribbons and threads of liquid enter the turbulent propellant gas region as the ribbons and threads are being shredded into fine particles. The ozone in the turbulent propellant gas comes into intimate contact with the fine particles as they are created and are collapsing into spherical droplets, thus promoting the absorption of the ozone into the fine particles.

**16 Claims, 4

ODOR CONTROL ATOMIZER UTILIZING OZONE AND WATER

RELATION TO PREVIOUS INVENTIONS

This invention bears a distinct relationship to the following United States patents earlier issued to Darrel R. Resch and Elisha W. Erb, the co-inventors herein:

| | |
|---|---|
| U.S. Pat. No. 3,993,246 | "NEBULIZER & METHOD" |
| U.S. Pat. No. 4,018,387 | "NEBULIZER" |
| U.S. Pat. No. 4,161,281 | "PNEUMATIC NEBULIZER & METHOD" |
| U.S. Pat. No. 4,161,282 | "MICROCAPILLARY NEBULIZER & METHOD" |
| U.S. Pat. No. 4,261,511 | "NEBULIZER & METHOD" |
| U.S. Pat. No. 5,232,164 | "PRECISELY ADJUSTABLE ATOMIZER" |
| U.S. Pat. No. 5,337,962 | "PNEUMATIC ATOMIZER HAVING IMPROVED FLOW PATHS FOR ACCOMPLISHING THE ATOMIZATION OF LIQUIDS" |

BACKGROUND OF THE INVENTION

Ozone is an allotropic form of oxygen containing three oxygen atoms in the molecule. Ozone is unstable. Its half-life in air is about twenty minutes. Inasmuch as ozone may not be stored, in order to be usefully employed, it must be generated on site. As to the production of ozone in useful quantities, it may be generated by exposing dry air, or oxygen, to ultraviolet light, or to a high voltage electric field that is corona discharging at the surface of the conductors.

Ozone, if dispersed in air, will oxidize any organic or inorganic impurities present in the air that are susceptible to being oxidized. If the impurity is an organic compound, and the oxidization process runs to completion, the impurity will be reduced to carbon dioxide and water. The propensity of ozone dispersed in air to oxidize impurities in the air has in the past been utilized for removing odoriferous impurities from air.

There are several advantages to using ozone to remove odors from air. The principal advantage is the simplicity of the process. All that is required is a closed chamber containing the air to be treated and an ozone generator. A second advantage involving the use of ozone is that there are no filters that must periodically be cleaned and replaced inasmuch as the process does not utilize filters. A third advantage is the end products of ozone purified air generally are carbon dioxide and water, which are both harmless substances.

There are, however, several disadvantages to using ozone to remove odors from air. The principal disadvantages are that for airborne ozone to be an effective odor control agent, the ozone must be present in the air to be treated at a concentration of about 10 to 20 parts per million (volume), and the ozone must be approximately evenly dispersed throughout the air. Furthermore, the ozone concentration must be maintained until the odoriferous compounds in the air have been oxidized.

The length of time required to remove all odor from a volume of air will necessarily depend on the ozone concentration, the concentration of the odoriferous compounds in the air, and the nature of the compounds. The higher the ozone concentration in the air to be treated, the faster odors will be removed from the air. Continuous efforts are required, however, to maintain a desired concentration of ozone in the air, because ozone's half-life in air is about twenty minutes. The output of an ozone generator may be directed into a chamber containing air, but because half the ozone in the chamber will break down into molecular oxygen ($O_2$) in about twenty minutes, the maximum amount of ozone that can be achieved in the chamber will be approximately one-half the amount of ozone made by the ozone generator during the period of one hour.

To obtain a desired concentration of ozone in the chamber, the chamber must be of such size that the amount of ozone generated by the ozone generator during half an hour, when mathematically divided by the amount of air in the chamber, equals the desired ozone concentration. If the chamber containing the air to be purified is large compared to the output of the ozone generator, the ozone concentration in the chamber will remain low, regardless of how long ozone is directed into the chamber from an ozone generator.

Other disadvantages to using airborne ozone to remove odoriferous compounds from air are associated with the fact that an ozone concentration that is sufficiently high to remove odors from air within a reasonable period of time is not safe for breathing. The Environmental Protection Agency has established an airborne ozone concentration of 0.5 parts per million (volume) as the safe upper limit for breathable air.

Another disadvantage to using airborne ozone to remove odoriferous compounds from air involves a time factor, for several minutes to an hour or more of reaction time is typically required for the desired result to be achieved. The required reaction time will depend on the ozone concentration and the nature of the odorous compounds in the air. Also, a "cooling down" period may have to follow the reaction period, during which the ozone concentration is allowed to decay to less than 0.5 parts per million, so as to below the safe upper limit for breathable air.

Still another disadvantage to using airborne ozone to remove odoriferous compounds from air is that a batch type process rather than a continuous flow of air process is involved, thus limiting this procedure to tasks such as deodorizing a room that may be sealed for a few hours, or for use in a confined area where humans normally would not be present, such as the lift chamber of a sanitary sewer lift station.

Ozone is soluble in water. Ozone reacts with water to form hydrogen trioxide ($HO_3$) and hydroxide (OH), which in turn react to form hydrogen dioxide ($HO_2$). Both hydrogen dioxide and hydroxide are strong oxidizers. They each react with many impurities, including microorganisms, such as bacteria and virus, destroying the impurity by oxidizing it. The possible achievement of these advantages readily explains why ozone is now commonly injected into municipal water supplies as a purifier and disinfectant.

If ozone is dissolved into water and the resulting mixture is sprayed into air as a fine aqueous mist, the ozone/water combination will almost immediately remove all odors from the air. The process is synergistic. Dissolving a given amount of ozone into water and then spraying the ozone containing water into a given amount of air will remove odors from the air many times faster than spraying pure water into the air or flowing the same amount of ozone directly into the same amount of air. The reaction is very fast because the ozone dissolved into the water reacts with the water to form hydrogen dioxide and hydroxide. Hydrogen dioxide and hydroxide, both of which are oxidizers, react very fast at the surface of the water spray's water droplets with any impurities in the air.

It is important to understand that spraying water containing dissolved ozone into air as very fine droplets as a means for removing impurities in the air has some major advantages over simply flowing ozone into the air to be purified. The reaction between the spray and any impurities in the air is very quick. The odor removal process may, for example, be carried out in a duct carrying a continuous flow of air to be purified. Also, because ozone, upon dissolving into water, reacts quickly with the water to form hydrogen trioxide and hydroxide, which in turn react to form hydrogen dioxide, there is little ozone remaining in the water to bubble out of the spray. This serves to alleviate concerns that the treated air might be a health hazard because of it containing in excess of 0.5 parts per million of ozone.

In order to be able to spray fine droplets of water containing ozone into the air in order to remove impurities from the air, it is necessary to first cause ozone to be absorbed in proper quantities into the water to be sprayed. Ozone can be dissolved into water by bringing gaseous ozone into contact with the water. The speed with which a given quantity of gaseous ozone will be absorbed by water depends on several factors, one being the size of the contact surface between the gaseous ozone and the water. The greater the contact area, the greater the speed at which the ozone is absorbed by the water.

A fine spray of liquid has a very large surface area for the volume of liquid contained in the spray. Ozone may be quickly dissolved into water by spraying a fine spray of water into an atmosphere containing ozone. The total surface area of the fine water droplets increases as the size of the water droplets decreases. Ozone in an atmosphere into which fine water droplets are being sprayed will be removed from the atmosphere and dissolved into the water droplets very quickly if the water droplets are very small and there is churning contact between the atmosphere and the water droplets.

The pneumatic atomizers of Erb and Resch, U.S. Pat. No. 3,993,246; Erb and Resch, U.S. Pat. No. 4,018,387; Erb and Resch, U.S. Pat. No. 4,161,281; Erb and Resch, U.S. Pat. No. 4,161,282; Erb and Resch, U.S. Pat. No. 4,261,511; Erb and Resch, U.S. Pat. 5,232,164 and Erb and Resch, U.S. Pat. No. 5,337,962 all involve elements that produce a thin liquid filaments or thin liquid ribbons and introduce the thin ribbons or filaments to an adjacent high speed flow of propellant gas. The thin ribbons or filaments of liquid are entrained into the flowing gas as thin ribbons or filaments of liquid, that are drawn out into elongated ribbons and threads that break up into smaller ribbons and threads of liquid, that in turn are drawn out and elongated by the propellant gas and break up into even smaller ribbons and threads. The foregoing drawings out, elongating and breaking up of the threads and ribbons of liquid repeats and continues until the liquid is in very small threads, ribbons, and irregular particles, which very small threads, ribbons and irregular particles collapse into spherical droplets. All of the foregoing takes place in the above identified pneumatic atomizers slightly downstream in the flowing propellant gas from the location where the thin liquid ribbons or filaments of liquid are introduced to the propellant gas.

It is of course known that a spherical liquid droplet has a smaller surface area than the same volume of liquid in any other shape. For example, a drop of liquid in the form of a thread has greater surface area than the same drop has after the drop has collapsed into a spherical droplet. The liquid in the thin ribbons or filaments of liquid entrained in the propellant gas flowing out of the above identified pneumatic atomizers has its greatest surface-area-to-volume ratio where the small threads, and ribbons of liquid described above are breaking up into irregular particles, which irregular particles collapse into small spherical droplets. The place where that occurs in the above-identified pneumatic atomizers is slightly downstream in the flowing propellant gas from the location where the thin liquid ribbon or filament is introduced to the flowing gas. The fact that the greatest surface-area-to-volume ratio of the liquid being atomized occurs slightly downstream in the flowing propellant gas from where the thin liquid ribbon or filament is introduced to the flowing gas is important to the instant invention because gas absorption into a liquid can only occur on the surface of the liquid, and the greater the surface area of a given quantity of liquid, the faster the gas is absorbed into the liquid.

A thread of liquid or any other irregular shaped particle of liquid has areas, many areas, that curve more acutely than the curve of the surface of a spherical droplet containing the same volume of liquid. The parts of the surface of the liquid thread or irregular particle with such acute curves are unstable. The surface tension forces acting on the surface of the liquid in such areas and the internal pressure forces of the liquid in such areas are not balanced. This imbalance is the source of the force that causes a thread or irregular particle of liquid to collapse into a sphere. This is important to the subject invention because it appears that a gas, such as ozone, if introduced to the ribbons, threads or irregular particles of liquid that exist in the above-identified pneumatic atomizers just downstream from where the filament of liquid is introduced to the flowing propellant gas, will be rapidly absorbed into the ribbons, threads and irregular particles of liquid. This absorption will occur much faster than otherwise because of the aforementioned imbalance.

If the objective of the instant invention was simply to introduce ozone to water by means of a pneumatic atomizer with the intent that the water absorb ozone, and that the ozone-bearing water, in the form of fine droplets, be exposed to air to be decontaminated, the objective could have been achieved by using an already known pneumatic atomizer and causing the propellant gas to be a mixture of air and ozone. Such a method or device is not practical for introducing ozone into water by the use of a pneumatic atomizer inasmuch as ozone corrodes the surface of everything with which it comes into contact, excepting only very stable, non-reactive materials such as glass and certain stainless steels.

Thus it is to be seen that the highly corrosive nature of ozone makes it difficult to pressurize or propel ozone for use as the propellant gas in a conventional pneumatic atomizer, with it also being difficult to duct the ozone containing propellant gas to the pneumatic nozzle. Furthermore, a pneumatic nozzle used in this manner would need to be made from materials that ozone will not corrode, which of course represents a great challenge.

A second difficulty that prevents using a mixture of air and ozone as the propellant gas in known pneumatic atomizers is the ozone will be approximately evenly distributed throughout the propellant gas in such atomizers. Unfortunately, the region in the downstream propellant gas where the propellant gas breaks up the liquid into small droplets does not occupy the entire downstream flow of the propellant gas. Some of the propellant gas will bypass the region in which the liquid is being broken up into small droplets. The ozone in the propellant gas that bypasses the region where the liquid is being drawn out and broken into irregular particles will not be absorbed by the liquid. Not having been exposed to the liquid, this will result in undesired unabsorbed ozone downstream.

A third difficulty that prevents using a mixture of air and ozone as the propellant gas in known pneumatic atomizers is the propellant gas in many such atomizers exits the atomizer as an essentially smooth flow and is flowing as an essentially smooth flow where it breaks up the liquid into fine droplets. It is highly advantageous that there be turbulence in the propellant gas-ozone mixture where the propellant gas breaks up the liquid into small droplets because turbulence will cause the propellant gas-ozone mixture to come into churning contact with the small liquid droplets as they are being formed, resulting in the ozone in the propellant gas being in intimate contact with the liquid when the liquid is most receptive to absorbing the ozone.

The instant invention may be used to create fine droplets of water containing absorbed ozone being carried away from the device as a mist by a propellant gas that is essentially free of unabsorbed ozone, which mist may be directed into an atmosphere containing impurities in order that the impurities be removed.

The instant invention may also be used as an efficient means for mass transfer of ozone into water or other liquid by flowing water or the other liquid through the instant invention, and collecting the resulting fine droplets in a sump. An example of the foregoing use of the instant invention is the removal of metal ions from a solution by flowing the solution through instant invention, whereby the metal ions will be oxidized by the ozone absorbed into the solution as it passes through the invention. The resulting droplets are collected in a sump, and the oxidized metal ions are allowed to precipitate out of the solution.

The instant invention is particularly useful for removing what is commonly called sewer gas from air. Sewer gas is generated in sewer pipes by natural biological processes acting on domestic waste and reactions of industrial wastes. Sewer gas consists principally of hydrogen sulfide ($H_2S$) and organic and inorganic hydrocarbons. Sewer gas is naturally present at a sewer line's outlet, such as the receiving chamber of a waste water treatment plant or the receiving chamber of a waste water pumping station. If not controlled, the sewer gas will flow into the atmosphere, causing unpleasant odors downwind.

Waste water treatment systems currently in use control sewer gas by adding chemicals that prevent the occurrence of the natural processes that generate the sewer gas, such as Sodium Hydroxide (NaOH), to the waste water at or near the upstream end of a sewer line. This is necessarily expensive, because of the cost of the chemicals. Other known waste water treatment systems control sewer gas by using air scrubbers spraying solutions of chemicals. This procedure also is expensive because of the cost of the chemicals used in the solution, which must be constantly replenished.

In general, the waste water treatment industry has attempted to use ozone to control sewer gas, but without success because of limitations due to the short half-life of ozone, as discussed above, and because the industry has not in the past had an efficient, simple and low energy means for introducing ozone into water.

It was to overcome the manifest problems of the prior art that the various embodiments of the instant invention were evolved.

SUMMARY OF THE INVENTION

The instant invention involves a pneumatic atomizer or purification device that creates in unenclosed open space, so as to avoid corrosion difficulties discussed above, the following conditions:

within a propellant gas drawing out fine ribbons and threads of liquid and shredding them into fine particles of liquid which collapse into fine droplets, thereby conditioning the liquid for the prompt absorption of ozone;

ozone is present in the central part of the propellant gas flowing downstream of the device;

all of that part of the downstream flowing propellant gas that contains ozone is turbulent, thereby causing the ozone to be quickly and evenly dispersed throughout such region. The turbulent region of the flowing propellant gas is hereinafter called the "Turbulent Propellant Gas Region" and will be discussed in greater detail below; and the fine ribbons and threads of liquid enter the Turbulent Propellant Gas Region just as the liquid is being shredded into fine particles and collapsing into fine droplets, whereby the ozone in the Turbulent Propellant Gas Region comes into violent intimate contact with the fine liquid particles as the fine liquid particles are being formed, with resultant almost instantaneous absorption of the ozone by the fine liquid particles and almost total removal of the unabsorbed ozone from the downstream propellant gas.

This invention utilizing ozone in a fine liquid mist for the purification of air involves a device comprising a body member having an internal passage through which propellant gas is constrained to flow under pressure, with such internal passage forming an outlet at a downstream location in the body member. Means are provided in the internal passage for supplying limited quantities of liquid, typically water, into the propellant gas, with the introduction of the liquid into the propellant gas causing thin ribbons and threads of liquid to flow into and with the gas flowing out of the outlet. An ozone supplying conduit is disposed in a central location in the outlet, with the conduit arranged to emit ozone into the propellant gas near the outlet. The propellant gas flows around the ozone supplying conduit at a substantial velocity and thus draws ozone from the conduit and creates turbulence in the propellant gas downstream of the ozone conduit. The location of the outlet of the ozone emitting conduit is such with regard to the thin ribbons and threads that these thin ribbons and threads of liquid enter the turbulence as they are breaking up into fine particles. The ozone in the turbulent gas comes into intimate contact with the liquid as it breaks apart into fine particles, thus promoting the absorption of the ozone by the fine liquid particles and thereby creating a mist of ozone in a propellant gas that is substantially free of unabsorbed ozone, thus being suitable for injection into the air to be purified.

It is to be noted that the ozone is emitted from the ozone-supplying conduit into the center of the propellant gas flow at a lesser velocity than the velocity of the propellant gas, with the difference between the velocities of the ozone and the propellant gas causing the propellant gas in a small finite volume of space adjacent the outlet of the ozone-supplying conduit to spin and thus cause a substantially constant procession of spinning and swirling volumes of the gas and ozone mixture that enlarges and occupies a region of the propellant gas as they move downstream. The region we identify above as the "Turbulent Propellant Gas Region" is the region in which the foregoing constant procession of spinning and swirling occurs. Various means are utilized for providing a thin ribbon or thread of liquid adjacent the outlet from the body member, to which means a relatively small quantity of liquid is supplied. The flow of propellant gas in the vicinity of the thin ribbon or thread of liquid draws the thin ribbon or thread of liquid from the liquid supplying means into the propellant gas. The thin ribbon or thread of liquid, upon entering the propellant gas, is drawn out and elongated by the flowing propellant gas. The Turbulent Propellant Gas Region, the region containing the turbulent ozone-gas mixture, envelopes the thin ribbon or thread of liquid as it is being shredded into fine irregular shaped particles of liquid, which irregular particles collapse within the Turbulent Propellant Gas Region into fine spherical liquid droplets, with this serving to bring the turbulent propellant gas and ozone mixture in the Turbulent Propellant Gas Region into close, churning contact with such ribbons and threads of liquid as the ribbons and threads are shredded into fine irregular particles of liquid that collapse into fine spherical droplets. In a highly effective manner, the ozone is absorbed into the fine liquid droplets, with the ozone-containing droplets being entrained in the propellant gas. These droplets are thereafter introduced into the air to be purified, with the unabsorbed ozone being substantially removed from the propellant gas.

The outlet of the ozone gas conduit is positioned with regard to the thin streams and ribbons of liquid is positioned such that the place where the fine ribbons and threads of liquid break apart into irregular fine particles and collapse into fine droplets is within the aforementioned Turbulent Propellant Gas Region. The advantage of this arrangement is that the liquid is most receptive to absorbing the ozone while the liquid is being broken into fine particles and the fine particles are collapsing into spherical droplets. The ozone is readily absorbed into the liquid when the ozone is well dispersed throughout the region in which the liquid is breaking up into fine particles and is in churning contact with the liquid as the liquid is breaking up into fine particles. The result of causing the liquid to be most receptive to absorbing ozone and causing the ozone to be most receptive to being absorbed by the liquid, is most of the ozone is promptly absorbed by the liquid, leaving the downstream propellant gas substantially free of unabsorbed ozone.

The preferred embodiment of the invention for generating a thin ribbon or thread of liquid for introduction to the turbulent propellant gas-ozone mixture involves first and second closely spaced smooth surfaces, with an edge of the first surface being disposed closely adjacent the propellant gas flowing through the gas outlet in the manner of Erb and Resch U.S. Pat. No. 5,232,164 with the second surface set back from the edge of the first surface such that a filming surface is defined on the downstream side of the first surface. The pair of closely spaced smooth surfaces are disposed in a parallel relationship with a very small spacing existing between the surfaces. Means are provided for directing a thin ribbon of a suitable liquid onto the filming surface, which typically involves directing water under pressure into the space between the closely spaced smooth surfaces, such that the water emits as a thin film along the edge of the second surface and onto the filming surface which thin film is drawn across the filming surface toward the propellant gas flowing through the gas outlet. The ozone conduit passes through the center of the gas outlet and terminates just upstream of the location where, if it were extended further downstream, it would be wetted by the liquid in the propellant gas.

The instant invention may utilize other means for generating a thin ribbon or thread of liquid for introduction to the propellant gas as the propellant gas leaves the propellant gas outlet, such as that disclosed in Erb and Resch, U.S. Pat. No. 5,337,962 and Erb and Resch, U.S. Pat. No. 3,993,246.

As will be seen in considerable detail hereinafter, the present invention provides a highly effective method for purifying air utilizing a nozzle through which a suitable propellant gas flows at a relatively high velocity, with ozone gas being inserted into the flow of the propellant gas at a central location with regard to the out flowing propellant gas at a point that is slightly downstream of the outlet of the nozzle. This arrangement prevents the highly corrosive ozone coming into contact with the nozzle components and causes prompt turbulent mixing of the ozone with the propellant gas within a region of the propellant gas downstream from where the ozone is introduced into the Turbulent Propellant Gas Region. Means are provided in the nozzle for causing fine ribbons and threads of liquid to flow into the turbulent region, where the ribbons and threads of liquid are shattered into fine particles that collapse into spherical droplets while within the turbulent region, with the turbulent propellant gas-ozone mixture that is within the region being in churning contact with the liquid as the liquid droplets are being formed, such that the ozone in the mixture will be rapidly absorbed into the liquid droplets. The ozone laden liquid is then exposed as fine droplets to the air to be purified.

Now somewhat more specifically, it is to be seen that the preferred embodiment of our novel method for purifying air involves flowing a propellant gas through a nozzle, with ozone being supplied through a central conduit whose outlet is slightly downstream of the propellant gas outlet. Quite advantageously, the flow of propellant gas serves to induce ozone to flow out of the ozone conduit. This arrangement makes it unnecessary for the ozone to be pressurized, thus eliminating the pumping difficulty that would ensue if it was necessary to supply ozone under pressure to the ozone conduit. This arrangement also causes prompt downstream mixing of the ozone with the propellant gas within the Turbulent Propellant Gas Region. The propellant gas also draws the liquid to be atomized present at the edge of the propellant gas conduit into the propellant gas in such a manner that the liquid is drawn out as thin ribbons and threads. The place where the liquid is introduced to the propellant gas is so located with regard to the Turbulent Propellant Gas Region that the resultant thin ribbons and threads of liquid enter the Turbulent Propellant Gas Region just as the thin ribbons and threads of liquid are breaking apart into fine irregular liquid particles, so that the ozone comes into close turbulent contact with the liquid as the liquid is being atomized, resulting in highly efficient absorption of the ozone by the liquid. The fine irregular liquid particles collapse into spherical droplets and thereafter are dispersed in a highly effective manner into the air to be purified.

A further significant aspect of this invention involves a novel method for removing metal ions from a flowable solution comprising the steps of flowing ozone through a conduit, exposing the outflow of the ozone conduit to the flowable solution as the solution is being shattered by a propellant gas into fine droplets slightly downstream from the outlet of the ozone conduit, with the ozone being brought into churning contact with the fine droplets as they are being formed, whereby the ozone is absorbed into the solution and oxidizes the metal ions. The fine droplets are collected and the oxidized metal ions are precipitated out of the solution.

An additional aspect of this invention involves a novel method for absorbing ozone into water comprising the steps of flowing ozone through a conduit, exposing the outflow of the ozone conduit to water as the water is being shattered by a propellant gas into fine droplets slightly downstream from the outlet of the ozone conduit, with the ozone being brought into churning contact with the fine droplets as they are being formed, whereby the ozone is absorbed into the water. The fine droplets are subsequently collected.

It is a primary object of this invention to provide a nozzle of inexpensive construction that generates a fine, ozone-containing liquid mist carried in air that is essentially free of unabsorbed ozone, thus being highly suitable for deodorizing purposes.

Figure 2:
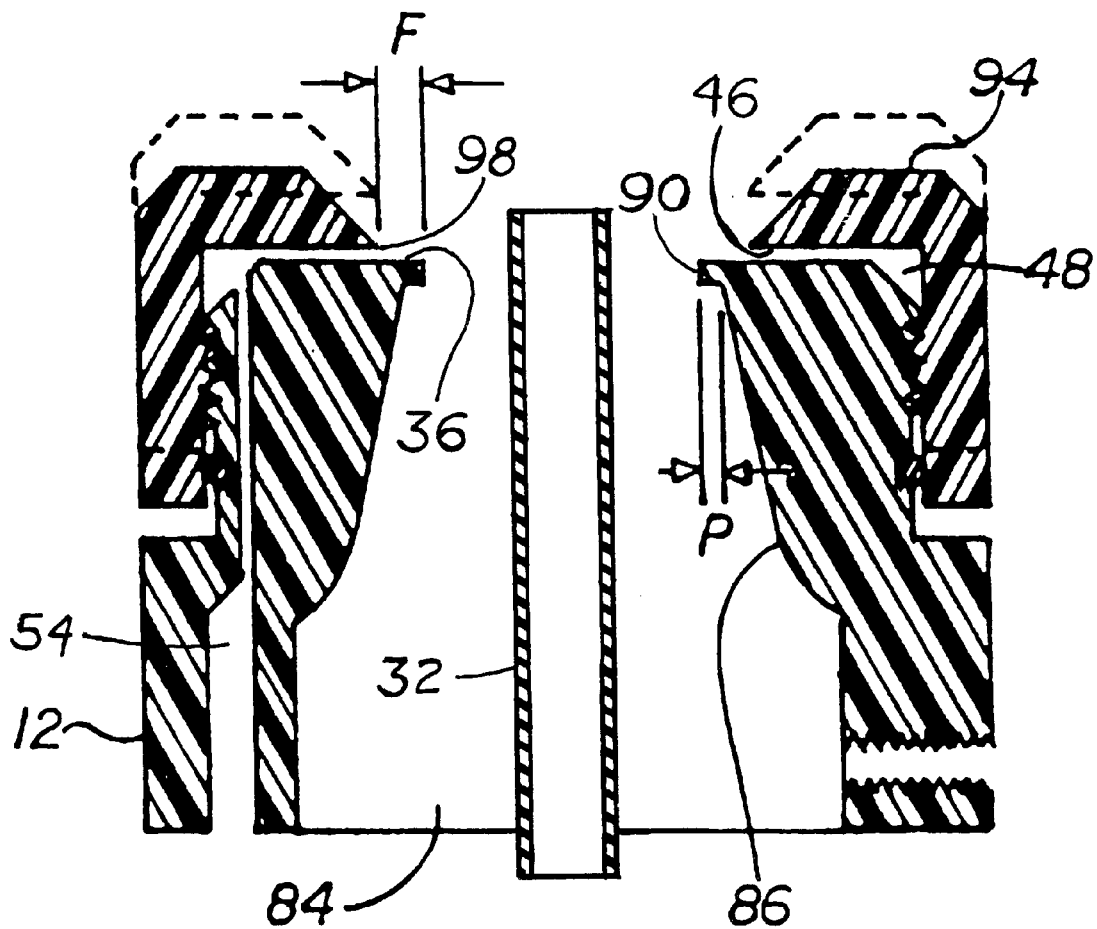

It is a more specific object of this invention to provide a multi-fluid nozzle utilizing a propellant gas under pressure that serves to provide a highly desirable mixing of ozone with at least some of the propellant gas, with the ozone being induced to flow from an ozone-supplying conduit located slightly downstream of the nozzle's outlet, thereby eliminating a need for any pumping to bring about the flow of ozone from the conduit and effectively preventing the corrosive effect of the ozone upon nozzle components. This arrangement induces downstream turbulence in the flowing propellant gas and thereby brings about a prompt distribution of the ozone and mixing with the propellant gas within the turbulent region.

It is a further object of our invention to provide a nozzle having an internal passage terminating in at least one outlet, through which passage a propellant gas is constrained to flow, with an ozone-supplying conduit located in the center of the gas flowing through the outlet slightly downstream of the outlet, with the flow of propellant gas through the outlet serving to entrain ozone and to cause a thorough mixing of the ozone with the propellant gas within the Turbulent Propellant Gas Region, with the ozone-containing gas thereafter coming into contact with ribbons and threads of liquid as they are drawn out and shredded into fine liquid particles that collapse into fine droplets, such that the droplets absorb the ozone and the ozone-containing droplets are entrained into the propellant gas and thereafter are introduced into the air to be purified.

It is a yet further object of the primary embodiment of our invention to define a device for purifying air by the use of ozone, with such device comprising a body member having an internal passage for the flow therethrough of a propellant gas, with an ozone-supplying conduit centrally located in the outward flowing propellant gas such that the propellant gas emitting from the body member will aspirate ozone from the conduit and mix intimately therewith in a region downstream of the ozone conduit, with the device also having a filming surface disposed closely adjacent the outward flow of propellant gas, upon which a thin film of water can be directed, with the flow of propellant gas drawing water from the filming surface into the propellant gas as ribbons and threads of liquid, which ribbons and threads enter the place where ozone and propellant gas are present, with the ozone in the propellant gas at such place being absorbed in a highly effective manner into the fine liquid droplets as the liquid is being atomized.

It is another object of this invention to provide a device for purifying air by the utilization of ozone provided in a fine liquid or aqueous mist, with this device comprising a body member having an internal passage for the flow of propellant gas therethrough, with this passage terminating in at least one outlet in which an ozone-supplying conduit is centrally disposed, with the propellant gas serving to draw ozone from the conduit and into the gas, with a constant procession of spinning and swirling volumes of the gas and ozone mixture tending to enlarge as it moves downstream, with a means for supplying a relatively small quantity of liquid into the propellant gas as thin ribbons and threads of liquid that are drawn out and shredded into fine irregular particles of liquid that collapse into fine droplets and also bringing the spinning and swirling mixture of propellant gas and ozone into churning contact with such ribbons and threads of liquid as the ribbons and threads are drawn out and shredded in fine irregular particles that collapse into fine droplets, with the ozone being absorbed into the fine liquid droplets, which ozone-containing droplets are entrained into the propellant gas and thereafter introduced into the air to be purified.

These and other objects, features and advantages will become more apparent as the description proceeds.

BRIEF DESCRIPTION OF DRAWINGS

FIG. 1 is a view of a primary embodiment of our novel device for purifying air by the use of ozone, with this embodiment being illustrated partly in section in order to reveal significant internal construction;

FIG. 2 is a cross-sectional view of the throat section of the primary embodiment of our invention, including the filming surface as well as the centrally disposed ozone-supplying conduit;

FIG. 3 is a large scale view revealing the important relationship of the interaction of ozone from the ozone-supplying conduit with the propellant gas flowing through the body member of our device and also revealing the region of turbulence in the propellant gas that we refer to as the Turbulent Propellant Gas Region, with the infusion of liquid into the ozone-gas mixture being deliberately omitted in this instance in the interests of clarity; and FIG. 4 is a view to a large scale illustrating how liquid such as water is drawn from the filming surface into the propellant gas as ribbons and threads of liquid, with this view also illustrating the area in which ozone-gas mixture is in churning contact with such ribbons and threads of liquid as the ribbons and threads collapse into fine droplets, with the ozone being absorbed into the fine liquid droplets preparatory to being introduced into the air to be purified.

DETAILED DESCRIPTION

With initial reference to FIG. 1, it will there be seen that we have revealed a principal embodiment of our invention, involving a device 10 provided for the purification of air by utilizing ozone contained in a fine liquid mist. The device 10, which involves a presentation of the components of our device in an exploded relationship, involves the utilization of a body member 12 having an internal passage or gas conduit 14 through which propellant gas is constrained to flow. This internal passage 14 is configured to form a converging type nozzle 16 that accommodates the flow of air or some other gas able to properly serve as a propellant gas.

The gas conduit 14 has an outlet 20 passing through a pair of closely spaced smooth surfaces, first surface 36 and second surface 46, and terminates adjacent the first surface 36. The smooth surfaces 36 and 46 are disposed in a parallel relationship, with a very small spacing existing between the surfaces as will be apparent from an inspection of FIG. 2.

The first smooth surface 36 is disposed in a substantially perpendicular relationship to the gas outlet 20, with an edge of the first surface 36 being disposed closely adjacent the propellant gas flowing through the gas outlet 20. The circularly configured edge of the second smooth surface 46 is set back from the circularly configured edge of the first surface, as made clear in FIG. 2, such that a filming surface F is defined on the downstream side of the first surface 36, adjacent the radially inward edge of the first surface; note FIGS. 2 through 4. The importance of the positioning of the filming surface F will be made clear hereinafter.

Also to be noted in FIGS. 1 and 2 is an ozone-supplying conduit 32 centrally disposed within the gas outlet 20, with the conduit 32 serving the function, basic to this invention, of emitting ozone at a desired location within the gas flowing through the gas outlet. It is most important to note that the outlet of conduit 32 is located slightly downstream of the gas outlet 20 and the filming surface F.

This particular location of the outlet of the ozone-supplying conduit is highly desirable for two reasons, the first being it is intended that the ozone come into association with the propellant gas as the propellant gas exits from the exterior of the nozzle. The reason for this construction is that if the ozone were to come into association with the propellant gas within the shell of the nozzle, the ozone gas would likely come into contact with parts of the nozzle and cause the corrosion thereof. This is of course distinct from known prior art pneumatic atomizers wherein it is frequently customary for a within-the-shell-of-the-nozzle contact to exist between the gases passing through the nozzle.

The second reason that having the outlet of the ozone-supplying conduit outlet be centrally disposed within the gas outlet 20 slightly downstream is that if the outlet is at this location it will cause what may be regarded as the central part of the propellant gas downstream of the outlet to be turbulent, which is important to the instant invention and will be discussed at length hereinafter. The particular placement of the outlet of the ozone-emitting conduit 32 with respect to the nozzle is a key feature of this invention and will of course be discussed as the description proceeds.

With regard to the basic construction of the device 10, it will be seen in FIG. 1 that the body member 12 may be secured, for example, to a conduit or supply duct 18 through which air or another gas under relatively low pressure may be supplied to the converging nozzle 16 of the body member 12. The securing of the body member to the conduit or duct may be accomplished by the use of one or more lock screws 19.

Relatively fine external threads 22 encircle the upper exterior portion of the body member 12. These external threads 22 are designed to receive an internally threaded cap 24, whose internal threads 26 are created so as to engage the threads 22 when the cap 24 is screwed onto the body 12. Inasmuch as for reasons of clarity, we have shown the cap 24 in an exploded relationship to the body member 12 in FIG. 1, it will be readily seen that there is a central hole or aperture 40 in the cap 24 that is essentially in alignment with the internal passage 14 in the body 12, and with the converging nozzle 16 and the gas outlet 20.

An O-ring 34 is mounted in a suitable circumferential indentation on the body 12, to assure a fluid-tight seal between the body 12 and cap 24. Note in FIG. 1 the preferable placement of the O-ring 34 below the threads 22, at a location in which it will be inside the skirt position 28 of the cap 24. FIG. 2 should be noted in this regard, wherein the cap 24 is shown in assembled relation on the body 12.

It will be readily observed from FIG. 1 that the previously mentioned toroidally-shaped smooth surface 36 extends entirely around the gas outlet 20 of the body 12, and is smooth. The innermost portion of the smooth surface 36 resides upon a small, abrupt jut into the internal or gas conduit passage 14, and is perpendicular thereto. We prefer to regard this part of the gas outlet 20 as a sharp edge orifice 30. The relationship of the peripheral contour of the orifice 30 to the generally columnar flow of propellant gas through this orifice will be discussed at length hereinafter.

It is also apparent from FIG. 1 that a steeply angled surface 42 extends entirely around the outer periphery of the flat, toroidally-shaped surface 36, with the upper edge of the angled surface 42 terminating at the outer periphery of the toroidal surface 36, and the lower edge of the angled surface 42 terminating near the upper edge of the previously mentioned external threads 22.

Around the upper interior portion of the cap 24 is what has been previously identified as the second smooth, toroidally-shaped surface 46, this latter surface being parallel to the first surface 36, as mentioned earlier. The surface 46 is of course able to be brought into close contact with the first surface 36 at such time as the cap 24 has been screwed relatively tightly onto the body member 12, with its threads 26 engaging the threads 22 on the body. FIG. 2 reveals the first toroidally-shaped surface 36 and the second toroidally-shaped surface 46 in a very close, parallel relationship during operation of this device, typically spaced apart between 0.002 and 0.020 inches. Also revealed in FIG. 2 are passage 84 and nozzle 86, through which the propellant gas is constrained to flow.

Also to be noted in the principal embodiment of our invention illustrated in FIG. 1 is inlet 54, disposed on the sidewall of the body member 12, by means of which liquid is admitted to the body. If our device is being utilized for odor control or to purify water, water is the liquid we utilize. If the invention is being used to remove ions from a liquid, another liquid may be used instead of water.

The liquid admitted to inlet 54 travels through upwardly ascending passage 56 that terminates in an opening 58 located con the previously mentioned angled surface 42. The liquid is then extruded onto the first surface 36 at a location interior of the cap 24. The column of propellant gas flowing through the converging nozzle 16 serves to pick up ribbons and threads of liquid flowing from between the surfaces 36 and 46 and onto the previously-described filming surface F.

It is to be understood that a radially inward flow of fluid from the opening 58 is intended to take place from between the surfaces 36 and 46 when these surfaces have been brought closely together, so the fact that the distance between the surfaces can be precisely changed by careful rotation of the cap 24 with respect to the body 12 is of significance. We prefer to use threads on the inside surface of the cap 24 that are sufficiently fine that one-half turn of the cap 24 changes the spacing between the surface 36 and 46 by only 0.020 inches.

To aid the precise setting of the cap 24 with respect to the body 12, we provide calibrations 50 that in FIG. 1 are to be seen at carefully spaced locations around the skirt 28 of the cap 24, which calibrations are to be used in conjunction with a mark or reference point 52 placed at an appropriate location on the body 12. This arrangement makes it readily possible for the operator or user to closely control the extruding of a flowable liquid between the surfaces 36 and 46, toward the internal passage 14 through the body 12, where the column of propellant gas flowing through the converging nozzle 16 serves to pick up the ribbons and threads of the liquid flowing onto the filming surface F.

The molecules of every liquid adhere one to another to some extent. This mutual adhesion is what prevents the liquid being a gas and dissipating. When some of the liquid on surface 36 near the central, sharp edge orifice 30 is drawn off surface 36 by the propellant gas, the adhesion of the liquid being drawn off with the remaining liquid on the surface 36 draws the remaining liquid toward orifice 30, with each molecule of liquid on surface 36 pulling the molecule of liquid radially behind it toward orifice 30. The liquid on surface 36 would draw liquid out from within the space between surfaces 36 and 46 if it were not for capillary attraction, the propensity of the liquid's molecules to adhere to some extent to surfaces 36 and 46, and therefore want to stay in the space between surfaces 36 and 46. If surface 36 and 46 are set sufficiently close to each other, the effective strength of the liquid's capillary attraction to such surfaces will be stronger than the effective strength of the mutual adhesion of the liquid to itself drawing the liquid across surface 36, with the result that liquid will be available for being drawn across the filming surface F only at the rate at which liquid is expressed from between surfaces 36 and 46 by the push of the liquid being supplied through inlet 54.

Figure 4:
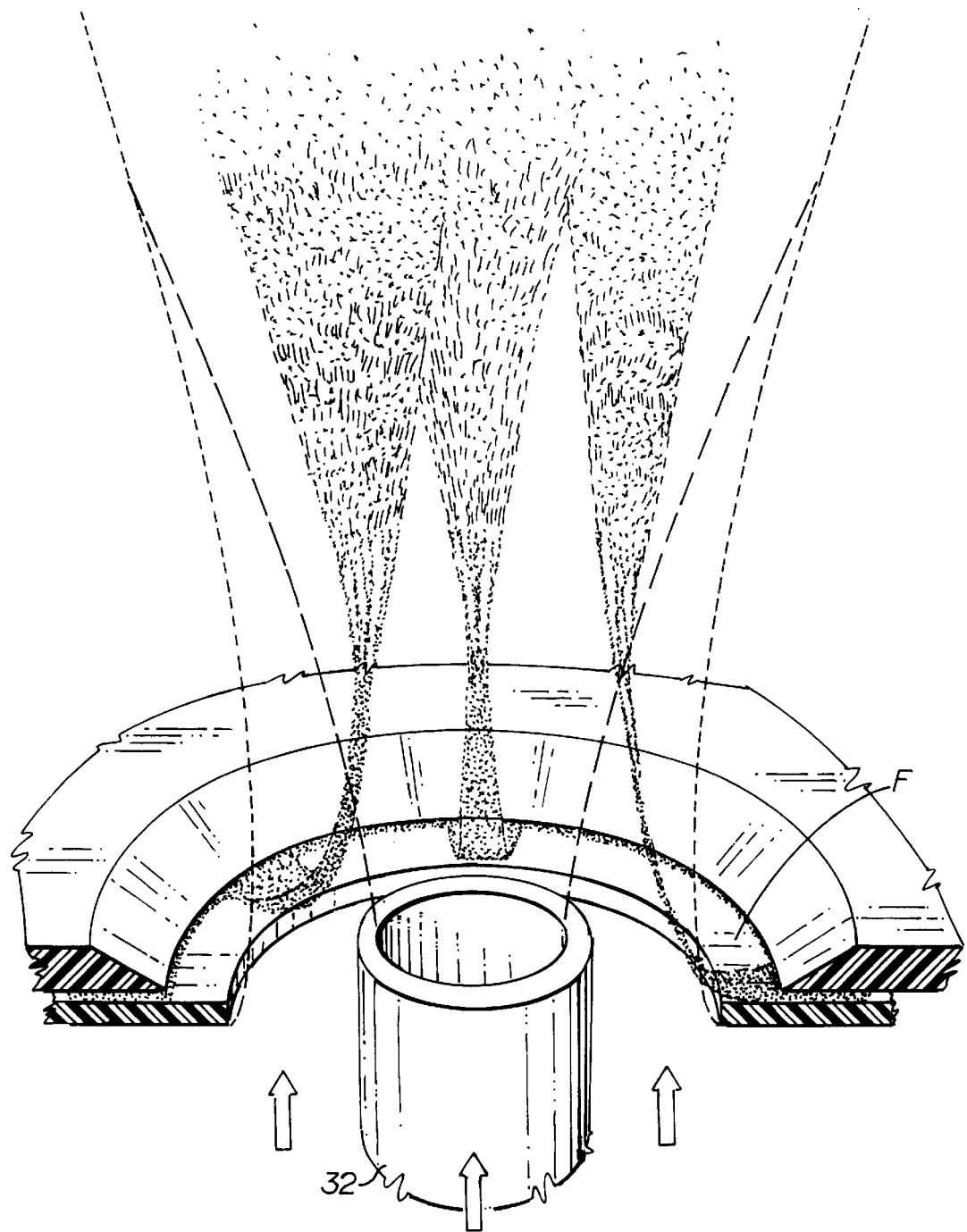

Liquid is not drawn out from within the space between abutting parallel surfaces 36 and 46 if the two surfaces are set sufficiently close to one another. The consequence of the foregoing is, if the liquid is supplied through inlet 54 at a rate that is less than the rate at which the propellant gas is capable of drawing liquid from the entire inner edge of central orifice 30 in surface 36, the liquid is drawn, not pushed, across the filming surface, from the space between surfaces 36 and 46 to central orifice 30. As a result, the liquid crosses the filming surface F as distinct ribbons and threads, as shown in FIG. 4.

Further regarding the embodiment of our invention principally depicted in FIG. 1, we configure the interior of the cap 24 to have an enlarged portion extending around the full inner circumference of the cap, and because of the creation of the angled surface 42 on the upper edge of the body 12, we have in effect created a plenum 48 around the outer circumferential edges of the abutting parallel surfaces 36 and 46, which plenum is visible in FIG. 2.

We typically maintain the liquid pressure in plenum 48 on the order of 0.01 to 1 pounds per square inch, and as a result, the liquid is caused to be extruded between the closely spaced surfaces 36 and 46 at a rate determined by the tightness with which the cap 24 has been applied upon the body 12.

It is thus to be seen that we have provided in accordance with this preferred embodiment of our invention, an arrangement for directing a fluid, such as water under pressure, into the space between the abutting smooth surfaces 36 and 46 so as to cause the water to emit from between the abutting surfaces, from which place the liquid is drawn toward the propellant gas flowing through the gas outlet. From the foregoing it should be clear that this liquid is drawn as thin ribbons and threads across the filming surface F identified in FIG. 2.

With continuing reference to FIG. 2, it is to be noted that member 94 is a cross-sectional representation of a cap corresponding to cap 24 of FIG. 1. It is to be understood the innermost portion of the toroidal surface 36 is not covered by member 94, and it is appropriate to regard this non-covered surface as the previously-mentioned filming surface F. the member 94 has an undersurface corresponding to the toroidally-shaped surface 46 of the cap 24 illustrated in FIG. 1, and this undersurface may be regarded as the second radially extending surface. In the middle of the member 94 is a central orifice or aperture 98, which is noticeably larger than the diameter of the orifice 90.

Figure 3:
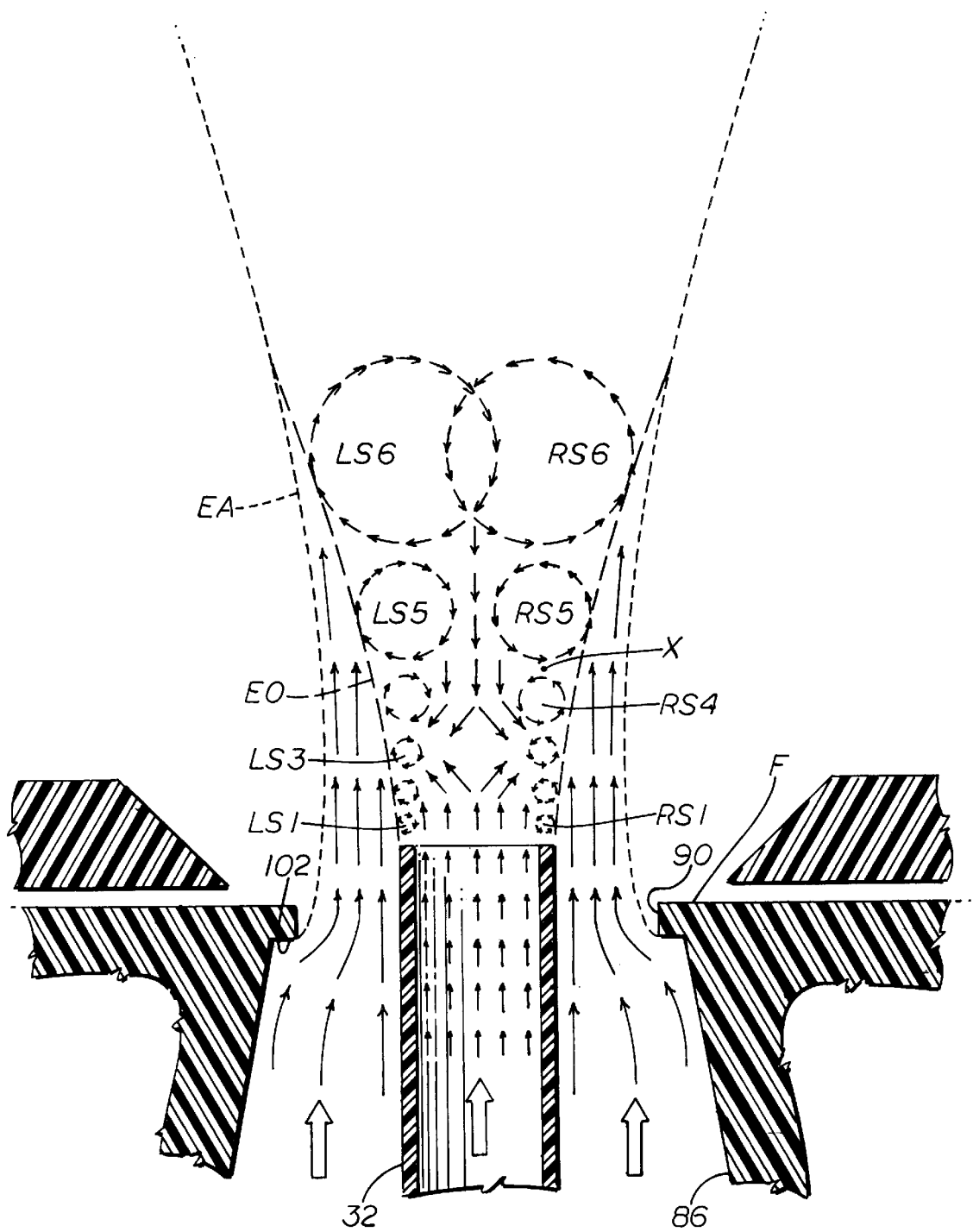

With particular reference now to FIG. 3, it is to be understood that the velocity of the gas flowing near the perimeter of the outlet of the nozzle 86 will be almost identical to the velocity of the gas flowing closer to the center of the nozzle outlet. Because the outlet's output immediately flows through the sharp edge orifice 90 that projects a short distance into the outlet of the nozzle, we have found that the velocity of the gas flowing near the perimeter of the orifice is almost identical to the velocity of the gas flowing closer to the center of the orifice.

The series of upwardly pointing arrows appearing in the circumferential portions of FIG. 3 may be regarded as representing the velocity and direction of the flowing propellant gas through the nozzle 86, with these arrows being all very nearly the same length to connote the substantially identical velocities of the propellant gas prior to the propellant gas coming into contact with the ozone.

It is to be noted that in FIG. 3 we utilize a configuration in which the orifice in the filming surface forms an abrupt small jut or projection 102 into the outlet from the nozzle. Quite advantageously, the provision of the sharp edge orifice 90 deflects the gas flow, as will be discussed at greater length hereinafter, but it does not to any consequential degree block the flow of gas through the orifice.

It is worthwhile to reemphasize in the instant atomizer depicted in FIG. 3, that the cross-sectional area and shape of the orifice 90 through the filming surface F is slightly smaller than the cross-sectional area and shape of the outlet of the converging nozzle 86, thereby forming the aforementioned lip or jut 102 that we regard as significant to this primary embodiment of this invention.

One of the important consequences of passing a fluid through a sharp edge orifice, with resulting deflection of the flowing gas, is the formation of a vena contracta. By definition, the cross-sectional area of the flow of the gas envelope EA, represented by a series of closely spaced dashes in FIG. 3, will be less at the vena contracta than the cross-sectional area at the orifice, and also less than the area at a downstream location in the gas flow. Because of the foregoing, the gas flowing through the sharp edged orifice 90 will desirably not come into direct contact with the sides of the orifice.

Applying the foregoing to the primary embodiment of this invention, if the sides of the orifice are sufficiently short, that is, the thickness of lip 102 is sufficiently thin in the flow direction depicted in the embodiment of FIG. 3, the gas flowing through the orifice 90 will not be in contact with the edge of the orifice as the flow exits the downstream side of the orifice. Therefore, because the gas exiting the filming surface side of the orifice 90 is not in contact with the sides of the orifice, the gas advantageously does not come into contact with the liquid lying on the filming surface F. Rather, the only liquid the flowing gas comes into contact with are the ribbons and threads of liquid that are being drawn from the filming surface F and entrained into the flowing gas.

Because the column of gas flowing out of the orifice 90 does not comes into direct, touching contact with the liquid on the filming surface F, the flowing gas in the representation of this embodiment advantageously does not cause the liquid on the filming surface to form what may be described as a highly undesirable rolling wave or ridge around the edge of the orifice.

From FIG. 3 it will be noted that the ozone-supplying conduit 32 is positioned near the center of the sharp edged orifice 90. The outlet of ozone conduit 32 is, quite importantly, slightly downstream in the propellant gas emanating from the orifice 90, but not so far downstream that it is wetted by the liquid being atomized by the device.

The series of upwardly pointing arrows in the interior of the ozone-supplying conduit 32 may be regarded as representing the velocity and direction of the flowing ozone, with these arrows being all very nearly the same length. It is important to understand that the arrows in the interior of the conduit 32 are much shorter than the propellant gas arrows depicted along the outside of the conduit 32 inasmuch as the ozone leaves the ozone conduit with much less velocity than the velocity of the propellant gas flowing through the nozzle 86 and the sharp edged orifice 90.

With regard to the gas in the small finite volume of space just above the lip of the ozone conduit 32, it is to be noted that we have identified a small volume of gas in FIG. 3 as LS1 (Left Swirl 1) just above the left side of the lip of the conduit, and as RS1 (Right Swirl 1) just above the right side of the lip of the conduit 32. The edge of the gas in the small finite volume of space that adjoins the ozone flowing out of the ozone conduit 32 is in contact with the relatively slow velocity ozone, whereas the edge of the gas adjoining the propellant gas flowing out of orifice 90 is in contact with the fast flowing propellant gas. The difference between the velocity of the ozone and the velocity of the propellant gas in contact with opposite sides of the gas in the small finite volume of space LS1 and RS1 causes the gas to spin. The spin of the gas in the small finite volume of space LS1 and RS1 is such that the gas closest to the lip of the conduit 32 is moving radially outward, whereas the gas in such volume furthest from the lip is moving radially inward. This is illustrated in FIG. 3 where small arrowheads associated with LS1 connote a clockwise spin, whereas the arrowheads associated with RS1, on the right side of the ozone conduit's outlet, indicate that the flow is counterclockwise.

The velocity of the ozone flowing out of the ozone conduit 32 and, more importantly, the velocity of the propellant gas flowing out of orifice 90 adjacent ozone conduit 32, both of which have contact with the spinning gas in the small finite volume of space, encourage the spinning gas to move downstream. This is represented on the left side in FIG. 3 by LS1, LS3, LS5 and LS6, and on the right side by RS1, RS4, RS5 and RS6.

As each spinning small volume of gas moves downstream it is replaced by a new volume of gas just above the lip of the ozone conduit 32, which replacement volume of gas starts to spin and move downstream, thereby causing a constant procession of swirling volumes of gas moving downstream from the outlet of the ozone conduit.

Most importantly, the continuing relatively slow velocity of the ozone on the radially inner side of the spinning and swirling gas and the relatively high velocity of the propellant gas on the radially outer side of the spinning and swirling gas causes the volume of the spinning and swirling gas to enlarge as it moves downstream, thus explaining why LS3 is larger than LS1, why LS5 is larger than LS3, and why LS6 is quite large. Tn the same manner, the volumes of gas on the right hand side continue to enlarge, with RS6 being much larger than RS1.

The effect of this phenomenon, involving the spinning and swirl ing gas, is to cause ozone to be directed radially outward and cause propellant gas to be directed radially inward, resulting in the creation of a highly desirable intimate mixture of ozone and propellant gas. As we have depicted by certain of the small arrows in FIG. 3, some of the ozone-gas mixture actually takes place in a reverse direction.

It should be understood that the creation of the spinning, swirling volumes of gas occurs in an ongoing manner, with each spinning and swirling volume of gas occupying only a small part of the perimeter of the space downstream from the ozone conduit's outlet, and then for only a moment or two before it is washed downstream in the flowing gas.

With regard to point "X" in FIG. 3, it will be noted that it is located a short distance downstream from the lip of the ozone conduit 32. It is exposed to the spinning and swirling volumes of gas described above as they move downstream. By way of example, location or point X will be exposed in one instance to gas flowing radially inward, and an instant later it will be exposed to gas flowing radially outward, as a spinning and swirling volume of gas passes over it. In a regularly recurring manner, location or point X will be exposed to gas flowing inwardly and then outwardly as the spinning and swirling volume of gas passes over this location.

We have found the most desirable location for the outlet of the ozone supply conduit 32 is in the center of the downstream flow of the propellant gas just upstream of where the ozone supply conduit would have been wetted by the liquid supplied to the propellant gas had the ozone supply conduit ended at a location further downstream.

In summary, there is much turbulence downstream of the outlet of the ozone conduit in the preferred embodiment of the instant invention. The turbulence is most desirable because it causes the rapid dispersal of the ozone flowing out of the ozone conduit into the propellant gas flowing out of orifice 90. It will be noted in FIG. 3 that we have utilized long dashed lines to connote an envelope EO to designate the region within the flowing propellant gas wherein the turbulence leading to the highly desirable mixture of ozone with the propellant gas takes place. We call the region within this envelope the "Turbulent Propellant Gas Region".

Tn the preferred embodiment of the instant invention, the liquid is drawn from the filming surface F into the propellant gas as thin ribbons and threads. The thin ribbons and threads of liquid enter the Turbulent Propellant Gas Region just as they are about to break apart into fine liquid particles and are buffeted by the turbulence therein, thereby bringing about, in a very dynamic manner, the thorough and intimate contact of the ozone in the gas in the Turbulent Propellant Gas Region with the thin ribbons and threads of liquid as the ribbons and threads of liquid are being drawn cut and broken into irregular fine particles and the irregular fine particles are collapsing into spherical droplets. This results in the prompt absorption of the ozone by the liquid and the substantially complete removal of unabsorbed ozone from the propellant gas. The turbulence in the propellant gas where the drawing out and breaking up of the threads of liquid into fine droplets occurs also promotes an even downstream distribution of the fine liquid particles in the gas flowing out of the preferred embodiment of the instant invention.

Turning now to FIG. 4, it will be seen that here we reveal to a somewhat larger scale, the relationship of the ozone-emitting conduit 32 to the gas outlet, with this figure making clear that the propellant gas, when flowing through the gas outlet, draws liquid from the filming surface F into the propellant gas as ribbons and threads of liquid, which ribbons and threads promptly enter the Turbulent Propellant Gas Region denoted by the long dashed lines of the envelope EO where ozone is present and where the ribbons and threads are shredded into fine particles that are evenly dispersed.

We have found that with the propellant gas flow drawing ozone from the ozone-emitting conduit 32, and the prompt turbulent mixing of the ozone with the propellant gas within the Turbulent Propellant Gas Region denoted by the long dashed lines of envelope EO, combined with the ozone and propellant gas mixture within the Turbulent Propellant Gas Region coming into churning contact with such ribbons and threads of liquid as the ribbons and threads are drawn out, shredded and collapse into fine droplets, results in the ozone being promptly absorbed into the fine liquid droplets. This also results in the substantial removal of unabsorbed ozone from the propellant gas, thereby producing a mist of ozone-containing droplets in a propellant gas that is substantially free of unabsorbed ozone, and thus ideally suited for introduction to air to be purified.

It is thus to be seen that we purify air in accordance with this invention by flowing propellant gas through the a gas orifice, and flowing ozone through a conduit that terminates at or slightly downstream of the orifice and in a central portion thereof, thereby creating turbulence in the flowing propellant gas downstream of the ozone outlet, with this turbulence causing the ozone and some of the propellant gas to become intimately mixed. The outlet of the gas orifice is surrounded with thin streams and ribbons of liquid being drawn into the propellant gas and shattered into fine droplets by the propellant gas at a location that is within the turbulent ozone-propellant gas mixture. As a consequence of this advantageous arrangement, the ozone-propellant gas mixture is brought into churning contact with the fine droplets as they are being formed, resulting in the prompt absorption of the ozone by the liquid droplets and the essentially complete removal of unabsorbed ozone from the propellant gas, which droplets are dispersed into the air to be purified.

We have found that this arrangement is highly effective for the purification of air in locations such as a pumping station for a sewer system.

It should be understood means other than the preferred embodiment described above may be used to supply the thin streams or filaments of liquid in the propellant gas and that such means may comprise a plurality of propellant gas orifices.

We claim:

1. A purification device utilizing ozone, said device comprising a body member having an internal passage through which propellant gas is constrained to flow under pressure, with said internal passage forming an outlet at a downstream location in said body member, means in said internal passage for supplying limited quantities of liquid into the propellant gas, with the introduction of the liquid into the propellant gas causing thin ribbons and threads of liquid to flow into and with the gas flowing out of said outlet and to break into fine particles, an ozone supplying conduit disposed in a central location in said outlet, with said conduit arranged to emit ozone into the propellant gas at a location near said outlet and to create a turbulent propellant gas region downstream of said ozone conduit, the propellant gas flowing around said ozone conduit at a substantial velocity and thus serving to induce the flow of ozone from said conduit, the position of the outlet of said ozone conduit with respect to the thin ribbons and threads of liquid being such that the thin ribbons and threads of liquid enter the turbulent propellant gas region as the ribbons and threads are being shredded into fine particles, the ozone in the turbulent propellant gas coming into intimate contact with the fine particles as they are created and are collapsing into spherical droplets, thus promoting the absorption of the ozone into the fine particles.

2. The purification device utilizing ozone as recited in claim 1 in which the liquid is water, and the fine particles generated by said device are utilized for odor control.

3. The purification device utilizing ozone as recited in claim 1 in which the liquid is water, and the fine particles generated by said device are collected in a sump.

4. The purification device utilizing ozone as recited in claim 1 in which the liquid is an acid into which metal has been dissolved.

5. The purification device utilizing ozone as recited in claim 1 in which said liquid contains metal ions.

6. The purification device utilizing ozone as recited in claim 5 in which the metal ions are removed from a solution by flowing the solution through the instant device and collecting the liquid in a sump, with the oxidized metal ions thereafter being precipitated out of the solution.

7. The purification device utilizing ozone as recited in claim 1 in which said means for supplying liquid into the propellant gas involves first and second closely spaced smooth surfaces, with an edge of said first surface being disposed closely adjacent the propellant gas flowing through said gas outlet, with said second surface set back from the edge of said first surface such that a filming surface is defined on the downstream side of said first surface, from which filming surface liquid is induced to enter the flow of propellant gas.

8. The purification device utilizing ozone as recited in claim 7 in which said ozone conduit projects through said propellant gas outlet and terminates downstream in the propellant gas flow just upstream of where said ozone conduit would be wetted by the limited quantities of liquid supplied to the propellant gas.

9. A purifying device utilizing ozone, said device comprising a body member having an internal passage through which propellant gas is constrained to flow, with said internal passage forming an outlet at a downstream location on said body member, an ozone-supplying conduit disposed in a central location in the propellant gas, with said conduit arranged to emit ozone into the propellant gas near said outlet, the propellant gas being pressurized so as to flow through said outlet and around said conduit at a substantial velocity, with the ozone being emitted from said outlet at a lesser velocity than the velocity of the propellant gas, the difference between the velocities of the ozone and the propellant gas causing turbulence in the propellant gas downstream of said conduit with resulting mixing of the ozone with the propellant gas, the turbulent propellant gas and ozone mixture spinning and swirling and enlarging as it moves downstream, means for supplying relatively small quantities of liquid adjacent said outlet, the flow of propellant gas past said liquid-supplying means drawing liquid into the propellant gas as ribbons and threads of liquid that are drawn out by the propellant gas and enter the propellant gas-ozone mixture where they are shredded into fine irregular particles that collapse into spherical droplets, the location of the outlet of said conduit being such relative to the drawn out threads of liquid that where the drawn out threads of liquid break apart into fine irregular particles and collapse into spherical droplets is within the spinning and swirling mixture of propellant gas and ozone, with the ozone being absorbed into the fine liquid droplets.

10. The purifying device utilizing ozone as recited in claim 9 in which the liquid is water, and the fine particles generated by said device are utilized for odor control.

11. The purifying device utilizing ozone as recited in claim 9 in which the liquid is water, and the fine particles generated by said device are collected in a sump.

12. The purifying device utilizing ozone as recited in claim 9 in which the liquid is an acid into which metal has been dissolved.

13. The purifying device utilizing ozone as recited in claim 9 in which said liquid contains metal ions.

14. The purifying device utilizing ozone as recited in claim 13 in which the metal ions are removed from a solution by flowing the solution through the instant device and collecting the liquid in a sump, with the oxidized metal ions thereafter being precipitated out of the solution.

15. The purifying device utilizing ozone as recited in claim 9 in which said means for supplying liquid into the propellant gas involves first and second closely spaced smooth surfaces, with an edge of said first surface being disposed closely adjacent the propellant gas flowing through said gas outlet, with said second surface set back from the edge of said first surface such that a filming surface is defined on the downstream side of said first surface, from which filming surface liquid is induced to enter the flow of propellant gas.

16. The purifying device utilizing ozone as recited in claim 15 in which said ozone conduit projects through said propellant gas outlet and terminates downstream in the propellant gas flow just upstream of where said ozone conduit would be wetted by the limited quantities of liquid supplied to the propellant gas.

* * * * *